US00PP26618P3

(12) United States Plant Patent
Dobres

(10) Patent No.: US PP26,618 P3
(45) Date of Patent: Apr. 19, 2016

(54) ***PEROVSKIA* PLANT NAMED 'NOVAPERLAC'**

(50) Latin Name: *Perovskia atriplicifolia*
Varietal Denomination: Novaperlac

(71) Applicant: CP DELAWARE, INC., Wilmington, DE (US)

(72) Inventor: Michael S. Dobres, Philadelphia, PA (US)

(73) Assignee: CP DELAWARE, INC., Wilmington, DE (US)

( * ) Notice: Subject to any disclaimer, the term of this patent is extended or adjusted under 35 U.S.C. 154(b) by 238 days.

(21) Appl. No.: 13/998,892

(22) Filed: Dec. 19, 2013

(65) Prior Publication Data

US 2015/0181791 P1 Jun. 25, 2015

(51) Int. Cl.
*A01H 5/00* (2006.01)

(52) U.S. Cl.
USPC ..... Plt./226

(58) Field of Classification Search
USPC ..... Plt./226, 263.1
See application file for complete search history.

*Primary Examiner* — Susan McCormick Ewoldt
*Assistant Examiner* — Karen Redden
(74) *Attorney, Agent, or Firm* — Buchanan Ingersoll & Rooney

(57) ABSTRACT

The new plant resulted as a mutation of a common plant of *Perovskia atriplicifolia* (unnamed and non-patented). The mutation was induced by exposing tissue cultured shoots to gamma irradiation and was followed by selection. Attractive purple blossoms are formed in abundance. A dense substantially upright compact growth habit is displayed. Sturdy branching is exhibited. The plant is well suited for providing attractive ornamentation in the landscape and has tended to blossom primarily in July through September.

1 Drawing Sheet

Figure 1:
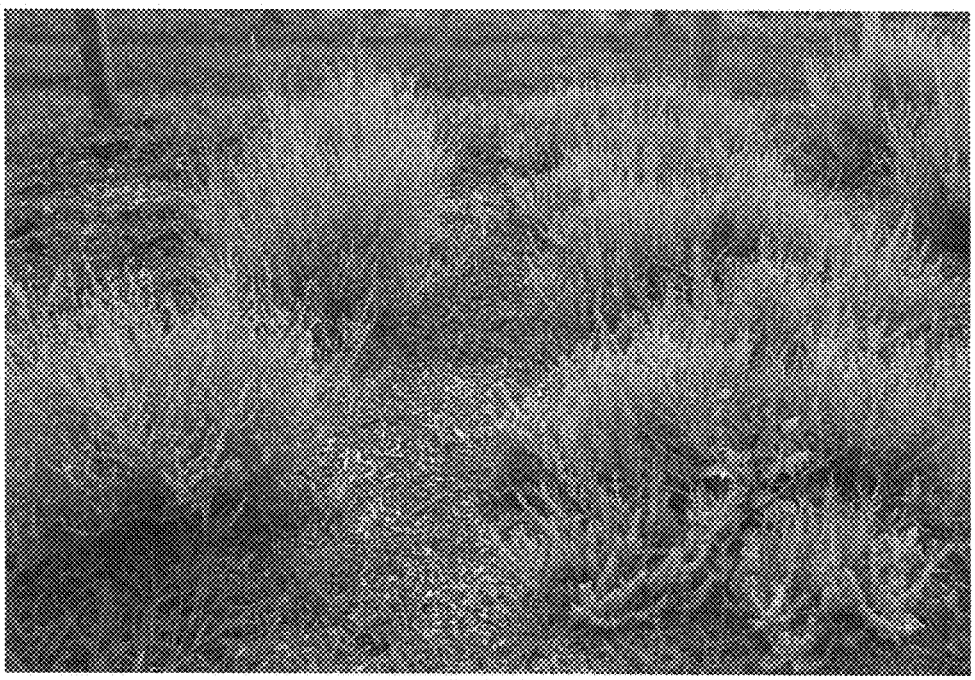

Botanical classification: *Perovskia atriplicifolia*.
Varietal denomination: cv. Novaperlac.

SUMMARY OF THE INVENTION

*Perovskia atriplicifolia* is an ornamental herbaceous perennial plant commonly known as Russian Sage.

The new plant of the present invention was derived by induced mutagenesis from a plant of the species *Perovskia atriplicifolia* (unnamed and non-patented). More specifically, on Oct. 26, 2006 tissue cultured shoots were subjected to gamma irradiation to yield a diverse population of plants that included many mutations which differed widely from each other. The irradiated shoots were rooted during July 2007, were transferred to soil, and were acclimatized during September 2007. The resulting plants were transferred to one-gallon containers in the spring of 2008, and were studied in detail at West Grove, Pa., U.S.A., for the possible presence of a novel attractive phenotype. A single plant of the present invention was selected and was preserved in view of its unique combination of attractive phenotypic characteristics. Had this plant not been created, identified and preserved it would have been lost to mankind.

It was found that the new *Perovskia* plant of the present invention displays the following combination of characteristics:

(a) exhibits a dense substantially upright growth habit,
(b) exhibits sturdy branching,
(c) displays finely-textured foliage,
(d) forms in abundance attractive purple blossoms, and
(e) is well suited for providing attractive ornamentation in the landscape.

During observations to date, the plant has been found to be hardy in U.S.D.A. Hardiness Zone No. 6. No further definitive hardiness information has been obtained.

The new cultivar well meets the needs of the horticultural industry and can be grown to advantage as a perennial garden plant to provide distinctive ornamentation. For instance, it can be grown in parks, gardens and residential settings.

Plants of the new cultivar in view of its combination of phenotypic characteristics can be readily distinguished from other *Perovskia* plants of the species, including its parent. More specifically, the new cultivar is significantly shorter than the parent plant, being about half the height of the *Perovskia atriplicifolia* (unnamed and non-patented) parent plant when grown in West Grove, Pa., U.S.A. Further, when compared to the 'Lisslitt' cultivar (U.S. Plant Pat. No. 20,845) in a side-by-side comparison at West Grove, Pa., U.S.A., the new cultivar was found to exhibit sturdier stems and a more upright growth habit.

The rooting of terminal cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novaperlac', and will be marketed under the LITTLE LACE Trademark.

BRIEF DESCRIPTION OF THE PHOTOGRAPHS

The accompanying photographs illustrate the new cultivar in color as nearly true as it is reasonably possible make the same in color illustrations of this nature. The plants were approximately one year of age and were being grown outdoors in full sun during July 2013 on their own roots at West Grove, Pa., U.S.A.

FIG. 1 illustrates specimens of typical mature flowering plants of the new cultivar at the left. The typical dense upright compact growth habit is shown. At the right is shown typical plants of 'Lisslitt' cultivar. Such 'Lisslitt' plants are shown to display less sturdy and less upright stems.

Figure 2:
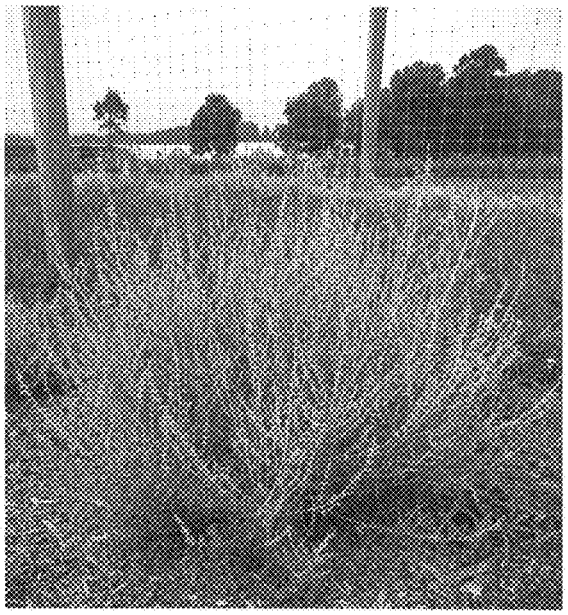

FIG. 2 illustrates another view of a typical flowering plant of the new cultivar.

DETAILED BOTANICAL DESCRIPTION

The following is a detailed description while observing two-year-old plants of the new cultivar that were produced by the rooting of cuttings. Such plants were being grown in one-gallon containers under greenhouse conditions at West Grove, Pa., U.S.A. The chart used in the identification of color is The R.H.S. Colour Chart (1995 Edition or equivalent) of The Royal Horticultural Society, London, England. Common color terms are to be accorded their customary dictionary significance.

Botanical classification: *Perovskia atriplicifolia*, cv. Novaperlac.

*Parent*.—Mutation of a common plant of *Perovskia atriplicifolia*.

*Plant type*.—Herbaceous perennial.

Plant:

*Growth habit*.—Dense substantially upright compact.

*Height*.—Approximately 30 to 35 cm on average when grown in a container.

*Spread*.—Approximately 30 to 35 cm on average when grown in a container.

*Branch length*.—Commonly approximately 30 cm on average.

*Stem diameter*.—Commonly approximately 3 mm on average.

*Stem color*.—Near Green Group 138C.

*Stem texture*.—Covered with somewhat stellate hairs.

*Stem quantity*.—Commonly approximately 17 stems per branch on average.

*Internode length*.—Commonly approximately 2 cm.

*Roots*.—Fibrous network, with the rooting of cuttings commonly commencing in approximately 21 days on average, and a fully rooted plant commonly being produced in approximately 46 days on average.

Foliage:

*Arrangement*.—Opposite.

*Shape*.—Elliptic to broadly lanceolate.

*Apex*.—Acute.

*Base*.—Cuneate.

*Length*.—Commonly approximately 4.2 cm on average.

*Width*.—Commonly approximately 1.7 cm on average.

*Aspect*.—Commonly approximately 45 degrees.

*Texture*.—Glabrous.

*Leaf quantity*.—Commonly approximately 50 leaves per branch on average.

*Color* (*young*).—On the upper surface near Green Group 137D, and on the lower surface near Green Group 138A.

*Color* (*mature*).—On the upper surface near Green Group 137A, and on the lower surface near Green Group 137C.

*Margins*.—Deeply and irregularly dissected with some dissections having multiple lobes measuring near 1 mm on average.

*Venation*.—Near Green Group 138A on the upper surface, and near Green Group 1388 on the under surface.

*Petiole*.—Commonly approximately 5 mm in length on average, approximately 1 mm in diameter on average, and near Green Group 137A in coloration on the upper surface and near Green Group 139C on the under surface.

Inflorescence:

*Flowering season*.—July through September with substantially continuous flowering primarily in August and September.

*Type*.—Commonly six-flowered vertillicasters arranged on terminal racemes, sessile.

*Buds*.—Ovoid, approximately 5 mm in length just before opening, approximately 2 mm in diameter, and near Violet-Blue Group 93B in coloration.

*Quantity*.—Very free-flowering, commonly with approximately 80 flowers per raceme during observations to date.

*Corolla shape*.—Bilabiate, tubular/campanulate, with upper lip four-toothed, and lower lip entire.

*Flower diameter*.—Approximately 8 mm on average.

*Flower depth*.—The tube length commonly is approximately 2 mm on average.

*Petal length*.—Approximately 3 mm on average.

*Petal width*.—Approximately 8 mm on average for the upper lip, and approximately 3 mm on average for the lower lip.

*Petal apex*.—Rounded.

*Petal margin*.—Entire.

*Petal texture*.—Glabrous.

*Petal color*.—When opening: the upper surface is near Violet-Blue Group 93C, and the lower surface is near Violet-Blue Group 94C. When open: the upper surface is near Violet-Blue Group 94B, and the lower surface is near Violet-Blue Group 93D.

*Sepal number*.—Five, fused at base.

*Sepal shape*.—Elliptic, tubular, campanulate.

*Sepal length*.—Approximately 5 mm on average.

*Sepal diameter*.—Approximately 3 mm on average.

*Sepal apex*.—Lanceolate.

*Sepal margin*.—Entire.

*Sepal texture*.—Commonly covered with short pubescence.

*Sepal color*.—Near Green Group 138B.

*Stamen number*.—Two.

*Anther shape*.—Ovoid.

*Anther size*.—Approximately 1 mm on average.

*Anther color*.—Near Violet Group 86D.

*Pollen*.—Present in a moderate quantity, and near Yellow-White Group 158D in coloration.

*Pistil length*.—Approximately 1.3 cm on average.

*Style length*.—Approximately 1 cm on average.

*Style color*.—Top portion is near Violet-Blue Group 92A, and the bottom portion is near White Group 155D.

*Stigma color*.—Near Violet-Blue Group 90D.

*Ovary color*.—Near Yellow-Green Group 144B.

*Seeds*.—No seed production has been observed to date.

*Fragrance*.—None observed.

Disease resistance: Believed to be typical to that of the species during observations to date.

Plants of the 'Novaperlac' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Perovskia atriplicifolia* plant having the following combination of characteristics:

(a) exhibits a dense substantially upright growth habit, (b) exhibits sturdy branching, (c) displays finely-textured foliage, (d) forms in abundance attractive purple blossoms, and (e) is well suited for providing attractive ornamentation in the landscape;

substantially as illustrated and described.

* * * * *